United States Defensive Publication [19] (H) [11] T100,401

Taylor [43] Mar. 3, 1981

[54] PROCESS FOR NEUTRALIZING SULFONIC OR SULFURIC ACID ESTERS WITH CALCIUM OR BARIUM BASES

[76] Inventor: Robert C. Taylor, 963 Longview Rd., King of Prussia, Pa. 19406

[21] Appl. No.: 114,933

[22] Filed: Jan. 24, 1980

Related U.S. Application Data

[63] Continuation of Ser. No. 61,800, Jul. 30, 1979, abandoned, which is a continuation of Ser. No. 869,393, Jan. 13, 1978, abandoned, which is a continuation of Ser. No. 697,511, Jun. 18, 1976, abandoned.

[51] Int. Cl.[3] ..... C07C 143/34; C07C 139/14; C07C 141/10; C07C 141/02

[52] U.S. Cl. ..... 260/505 N; 260/504 A; 260/458 R; 260/459 R; 260/460

[57] ABSTRACT

An improved method of preparing calcium or barium sulfonic acid or sulfuric acid ester salts is presented which comprises coneutralizing the corresponding sulfonic or sulfuric acid esters with a mixture comprised of a calcium or barium base and a base of an alkali metal, ammonia, or magnesium.

13 Claims, No Sheets Drawing,

16 Pages Specification

The file of this unexamined application may be inspected and copies thereof may be purchased (849 O.G. 1221, Apr. 9, 1968)